(12) United States Patent
Sims et al.

(10) Patent No.: US 11,439,683 B2
(45) Date of Patent: *Sep. 13, 2022

(54) ANTI-ANGIOGENIC THERAPY OF METASTATIC COLORECTAL CANCER

(71) Applicant: REGENERON PHARMACEUTICALS, INC., Tarrytown, NY (US)

(72) Inventors: Tasha Nicholle Sims, New York, NY (US); Bo Gao, Ringoes, NJ (US); Israel Lowy, Dobbs Ferry, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 326 days.

This patent is subject to a terminal disclaimer.

(21) Appl. No.: 16/690,459

(22) Filed: Nov. 21, 2019

(65) Prior Publication Data

US 2020/0129589 A1 Apr. 30, 2020

Related U.S. Application Data

(62) Division of application No. 15/509,461, filed as application No. PCT/US2015/049279 on Sep. 10, 2015, now Pat. No. 10,525,104.

(60) Provisional application No. 62/051,091, filed on Sep. 16, 2014, provisional application No. 62/099,630, filed on Jan. 5, 2015.

(51) Int. Cl.
| | |
|---|---|
| *A61K 38/17* | (2006.01) |
| *A61K 38/18* | (2006.01) |
| *G01N 33/574* | (2006.01) |
| *G01N 33/74* | (2006.01) |
| *A61K 45/06* | (2006.01) |

(52) U.S. Cl.
CPC ............ *A61K 38/179* (2013.01); *A61K 45/06* (2013.01); *G01N 33/57419* (2013.01); *G01N 33/74* (2013.01); *G01N 2333/475* (2013.01); *G01N 2800/52* (2013.01)

(58) Field of Classification Search
None
See application file for complete search history.

(56) References Cited

FOREIGN PATENT DOCUMENTS

| WO | WO 2011/089101 | 7/2011 |
|---|---|---|
| WO | WO 2012/010550 | 1/2012 |
| WO | WO 2012/146610 | 11/2012 |

OTHER PUBLICATIONS

Hayashi, et al., "Biomarkers of reactive resistance and early disease progression during chemotherapy plus bevacizumab treatment for colorectal carcinoma", Oncotarget. May 15, 2014;5(9):2588-95.
Hedge, et al., "Predictive Impact of Circulating Vascular Endothelial Growth Factor in Four Phase III Trials Evaluating Bevacizumab", Clin Cancer Res. Feb. 15, 2013;19(4):929-37.
Jurgenmeier, et al., "Prognostic and predictive value of VEGF, sVEGFR-2 and CEA in mCRC studies comparing cediranib, bevacizumab and chemotherapy", Br J Cancer. Apr. 2, 2013;108(6):1316-23.
Spratlin, et al., "Phase I Pharmacologic and Biologic Study of Ramucirumab (IMC-1121B), a Fully Human Immunoglobulin G1 Monoclonal Antibody Targeting the Vascular Endothelial Growth Factor Receptor-2", J Clin Oncol. Feb. 10, 2010;28(5):780-7.
Sun, et al., "Ziv-aflibercept in metastatic colorectal cancer", Biologies. 2014; 8: 13-25.
George et al., "VEGF-A, VEGF-C, and VEGF-D in Colorectal Cancer Progression" Neoplasia (2001) 3(5):420-427.

*Primary Examiner* — Christine J Saoud
*Assistant Examiner* — Jon M Lockard
(74) *Attorney, Agent, or Firm* — Thomas Triolo; Karl Bozicevic; Bozicevic, Field & Francis LLP

(57) ABSTRACT

The present invention provides methods for treating metastatic cancer comprising identifying subjects who will respond favorably to anti-VEGF therapy. According to certain aspects of the invention, subjects are identified based on their expression level of one or more predictive biomarkers. Favorable response to anti-VEGF therapy is indicated by high expression levels of certain biomarkers or by low expression levels of certain biomarkers. An exemplary predictive biomarker is VEGF-A. Also disclosed herein are prognostic biomarkers useful for identifying cancer-bearing subjects who are expected to have better relative survival outcomes.

8 Claims, 3 Drawing Sheets

Specification includes a Sequence Listing.

SEQUENCE LISTING

<160> NUMBER OF SEQ ID NOS: 2

<210> SEQ ID NO 1
<211> LENGTH: 1377
<212> TYPE: DNA
<213> ORGANISM: Artificial Sequence
<220> FEATURE:
<223> OTHER INFORMATION: VEGF Trap

<400> SEQUENCE: 1

```
atggtcagct actgggacac cggggtcctg ctgtgcgcgc tgctcagctg tctgcttctc     60
acaggatcta gttccggaag tgataccggt agaccttctcg tagagatgta cagtgaaatc    120
cccgaaatta tacacatgac tgaaggaagg gagctcgtca ttccctgccg ggttacgtca    180
cctaacatca ctgttacttt aaaaaagttt ccacttgaca ctttgatccc tgatggaaaa    240
cgcataatct gggacagtag aaagggcttc atcatatcaa atgcaacgta caagaaata    300 gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata gaaacttgt aaaccgagac    540 ctaaaaaccc agtctgggag tgagatgaag aaattttga gcaccttaac tatagatggt    600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct tcccccccaaa acccaaggac    780 accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 2
<211> LENGTH: 458
<212> TYPE: PRT
<213> ORGANISM: Artificial Sequence
<220> FEATURE:
<223> OTHER INFORMATION: VEGF Trap

<400> SEQUENCE: 2

Met Val Ser Tyr Trp Asp Thr Gly Val Leu Leu Cys Ala Leu Leu Ser

-continued

```
1               5                   10                  15
Cys Leu Leu Leu Thr Gly Ser Ser Gly Ser Asp Thr Gly Arg Pro
            20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
            50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                    85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                    165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205

Tyr Thr Cys Ala Ala Ser Ser Gly Leu Met Thr Lys Lys Asn Ser Thr
210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                    245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                    325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                    405                 410                 415

Leu Tyr Ser Lys Leu Thr Val Asp Lys Ser Arg Trp Gln Gln Gly Asn
            420                 425                 430
```

-continued

```
Val Phe Ser Cys Ser Val Met His Glu Ala Leu His Asn His Tyr Thr
            435                 440                 445

Gln Lys Ser Leu Ser Leu Ser Pro Gly Lys
    450                 455
```

ANTI-ANGIOGENIC THERAPY OF METASTATIC COLORECTAL CANCER

FIELD OF THE INVENTION

The present invention relates to the use of predictive and prognostic biomarkers in identification and treatment of metastatic cancer in patients.

BACKGROUND

Vascular endothelial growth factor (VEGF) is a cytokine involved in angiogenesis. The ligand VEGF-A interacts with VEGF receptor-1 (VEGFR1) and VEGFR2, thereby initiating an angiogenesis signaling pathway in normal and tumor vasculature. Antagonists of VEGF are known to be useful for the treatment of a variety of diseases and disorders including cancers, eye diseases and other conditions involving excessive, unwanted or inappropriate angiogenesis. An example of a VEGF antagonist is aflibercept (also known as VEGF Trap; or ziv-aflibercept, which is marketed as ZAL-TRAP®, Regeneron Pharmaceuticals, Inc., Tarrytown, N.Y.). Aflibercept is a VEGF receptor-based chimeric molecule comprising domain 2 from VEGFR1 fused to domain 3 from VEGFR2, which is, in turn, attached through the hinge region to the Fc(a) domain of human IgG1. Ziv-aflibercept is approved for the treatment of metastatic colorectal cancer and is being developed for the treatment of other cancerous conditions as well. VEGF Trap is described, e.g., in U.S. Pat. No. 7,070,959; see also, Holash et al., *Proc. Natl. Acad. Sci. USA* 99:11393-11398 (2002).

To date, no predictive biomarkers of resistance or susceptibility to VEGF inhibition have been validated. Although VEGF antagonists have shown great promise in the treatment of cancer, validated biomarkers that predict the efficacy of anti-VEGF therapy are needed for the effective identification and selection of patient sub-populations that respond favorably to anti-VEGF therapy. Accordingly, an unmet need exists in the art for identifying and validating predictive and prognostic biomarkers in patients with metastatic cancer who are administered anti-VEGF therapy.

BRIEF SUMMARY OF THE INVENTION

According to one aspect of the present invention, methods are provided for treating cancer in a subject. For example, the methods according to this aspect of the invention comprise administering a VEGF antagonist to the subject, wherein the subject has been diagnosed with metastatic cancer and has been selected for treatment with a VEGF antagonist on the basis of exhibiting elevated expression of a predictive biomarker such as VEGF-A. In certain embodiments, the elevated expression of the predictive biomarker is determined based on a comparison to lower level of biomarker expression in cancer-bearing subjects. In one embodiment, the metastatic cancer is metastatic colorectal cancer (mCRC).

According to another aspect of the present invention, methods are provided for treating advanced ovarian cancer in a subject. The methods according to this aspect of the invention comprise administering a VEGF antagonist to the subject, wherein the subject has been diagnosed with advanced ovarian cancer and has been selected for treatment with the VEGF antagonist on the basis of exhibiting variant (i.e., increased or decreased) expression of interleukin-6 (IL-6). In certain embodiments, variant expression of IL-6 in the subject is determined based on a comparison to the level of IL-6 expression in non-cancer-bearing subjects. Under circumstances in which a cancer patient is identified as exhibiting increased expression of IL-6, the patient may be effectively treated according to the present invention by administration of a combination of a VEGF antagonist and an IL-6 or IL-6 receptor antagonist.

According to another aspect of the present invention, methods are provided for identifying a subject with metastatic colorectal cancer who is likely to respond favorably to anti-VEGF therapy. The methods according to this aspect of the invention comprise obtaining a sample from the patient and measuring in the sample the level of a predictive biomarker such as VEGF-A (or other predictive biomarker(s) as described herein), wherein an elevated expression of the predictive biomarker as compared to the lower level of biomarker expression (identified as "high" level as disclosed elsewhere herein) in a patient with mCRC, identifies the patient as a patient who is likely to respond favorably to anti-VEGF therapy.

In some embodiments, the anti-VEGF therapy comprises administration of a VEGF antagonist to a subject in need thereof. The VEGF antagonist used with the methods of the present invention may be an anti-VEGF antibody, an anti-VEGF receptor antibody or a VEGF receptor-based chimeric molecule (VEGF Trap). In certain embodiments, the VEGF antagonist is ziv-aflibercept.

In some embodiments, the anti-VEGF therapy may be administered in combination with a chemotherapeutic agent and/or regimen. Exemplary chemotherapeutic agents/regimens include folinic acid, 5-fluorouracil and oxaliplatin (i.e., the FOLFOX treatment), and folinic acid, 5-fluorouracil and irinotecan (i.e., the FOLFIRI treatment).

In certain embodiments, the sample obtained from the patient is selected from the group consisting of blood, serum and plasma.

Other embodiments of the present invention will become apparent from a review of the ensuing detailed description.

DETAILED DESCRIPTION

Figure 1:
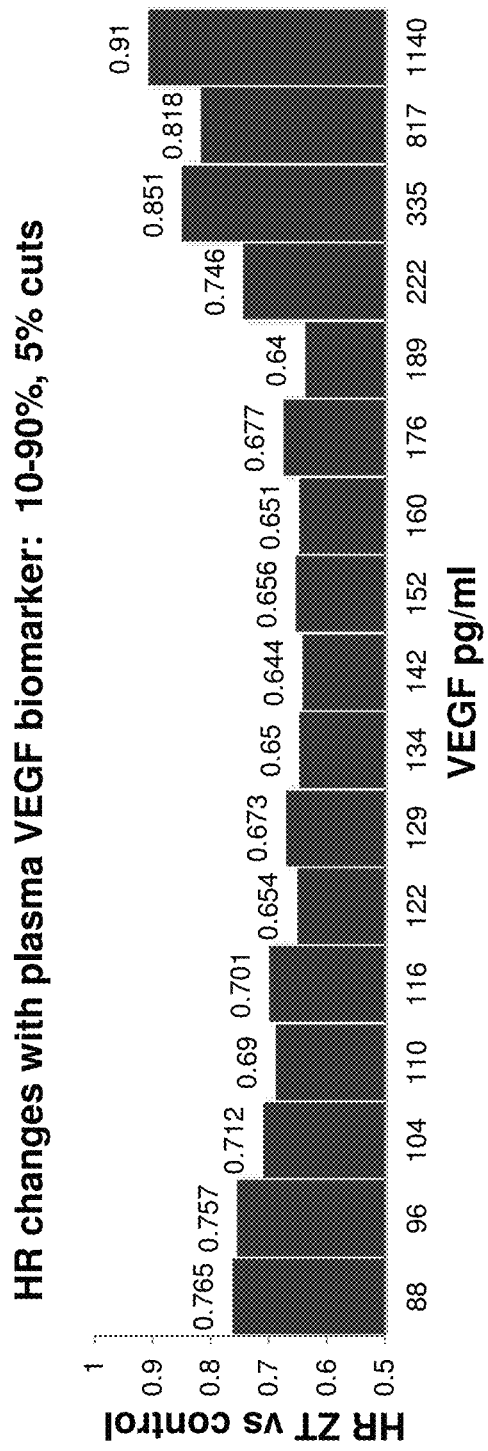
FIG. 1 is a graph of hazard ratio (HR) changes of the "high" biomarker group(s). The biomarker "high" group was defined by cutoff values ranging from 88 to 1140 pg/mL of plasma VEGF biomarker concentrations in a subset of patients with metastatic colorectal cancer (mCRC) in a phase 3 study of mCRC patients treated with aflibercept in combination with FOLFIRI.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Predictive and Prognostic Biomarkers

The present invention is based in part on the identification of certain biomarker proteins whose expression levels (higher or lower than median expression levels) in cancer patients were found to correlate with enhanced overall survival (OS) following treatment with an anti-angiogenic agent. In particular, certain protein biomarkers were identified that when expressed at higher or lower levels in patients with metastatic colorectal cancer (mCRC) correlated with enhanced overall survival of such patients following treatment with the VEGF antagonist ziv-aflibercept. An exemplary biomarker that can be used in the context of the present invention to identify patients likely to respond favorably to ziv-aflibercept treatment is VEGF-A. In certain embodiments, patients with higher levels of VEGF-A as compared to the level of VEGF-A expression in patients with mCRC and not treated with a VEGF antagonist, were found to have improved survival outcomes when treated with anti-VEGF therapy. In certain embodiments, increased or decreased expression of one or more biomarkers may be used as a component of a signature to identify patients likely to respond favorably to ziv-aflibercept treatment. For example, the signature may include VEGF pathway proteins (such as VEGF-R2 and VEGF-R3) or inflammation-related markers such as macrophage migration inhibitory factor (MIF) and surfactant protein D (SPD).

In a related aspect, the present invention relates to identification of certain protein biomarkers that when expressed at higher or lower than median levels in patients with advanced ovarian cancer correlated with enhanced overall survival of such patients following treatment with the VEGF antagonist ziv-aflibercept. An exemplary biomarker that can be used in the context of the present invention to identify patients likely to respond favorably to ziv-aflibercept treatment is the cytokine interleukin-6 (IL-6). In certain embodiments, patients with lower levels of IL-6 as compared to median level of IL-6 expression in patients with advanced ovarian cancer and not treated with a VEGF antagonist, were found to have improved survival outcomes when treated with anti-VEGF therapy.

As used herein, a "predictive" biomarker refers to a biomarker that gives information on the effect of a therapeutic intervention in a patient. The predictive biomarker may also be a target for therapy. A predictive biomarker can be used for patient selection, specifically, for identifying patients that will respond favorably to a particular therapy. In the context of the present invention, a predictive biomarker includes a protein biomarker with an elevated or reduced expression that correlates with improved survival outcome of a patient having cancer (such as metastatic colorectal cancer or ovarian cancer) and treated with anti-VEGF therapy as compared to a similarly situated patient not treated with anti-VEGF therapy. An example of a predictive biomarker, found in the study exemplified herein, is VEGF-A. A mCRC patient who had elevated expression of VEGF-A and was treated with ziv-aflibercept had a higher probability of overall survival as compared to a patient having mCRC but not treated with ziv-aflibercept. Another example of a predictive marker is IL-6. A patient with ovarian cancer who had elevated expression of IL-6 and was treated with ziv-aflibercept had a lower probability of overall survival as compared to a patient having ovarian cancer but not treated with ziv-aflibercept. Additional examples of predictive biomarkers include VEGF-R2, VEGF-R3, SPD and MIF. Certain biomarkers may be categorized as both predictive and prognostic. An example of a biomarker that may be classified as both predictive and prognostic in the context of cancer treatment with a VEGF antagonist is IL-8.

The present invention also relates to the identification of certain prognostic biomarkers that correlate with mCRC overall survival. Prognostic biomarkers include proteins that when expressed at higher or lower than normal levels in patients with metastatic colorectal cancer (mCRC) correlate with enhanced overall survival of the patients irrespective of treatment. Exemplary prognostic biomarkers that can be used in the context of the present invention to identify patients with potentially enhanced mCRC overall survival include angiopoietin-2 (Ang-2), C-reactive protein (CRP) and NRP1.

As used herein, a "prognostic" biomarker refers to a biomarker that provides information about a patient's overall cancer outcome, regardless of treatment. A prognostic biomarker may give information on recurrence in patients who receive curative treatment. In some embodiments, altered expression of a prognostic biomarker correlates with progression-free survival in a patient with metastatic disease. In the context of the present invention, the term "prognostic" biomarker refers to altered expression of a protein biomarker that correlates with poor prognosis of metastatic cancer in a patient. For example, it is shown herein that mCRC patients with high plasma Ang-2 or CRP levels had poor prognosis of mCRC (e.g., decreased probability of survival) compared to patients with low Ang-2 or CRP levels, whether the patients were treated with anti-VEGF therapy or not.

The level of predictive and prognostic biomarkers may be determined in a patient by directly or indirectly measuring the absolute or relative amount of the biomarker in a tissue sample, tumor sample (e.g., biopsy), or fluid sample obtained from the patient. The fluid sample may be selected from the group consisting of blood, plasma and serum. The amount of a biomarker may be measured in a sample using techniques such as enzyme linked immunosorbent assay (ELISA), or other protein detection and analytic methods, as well as by measuring the amount of nucleic acid (e.g., mRNA) that encodes the protein biomarker. Assays that involve directly measuring or detecting specific protein biomarkers in a sample can be accomplished using, e.g., antibodies or other antigen-binding proteins specific for the biomarker. Such antibodies or antigen-binding proteins can be labeled with a detectable compound such as a fluorophore or radioactive compound. Thus, the present invention also includes antibodies and antigen-binding proteins that specifically bind any of the predictive or prognostic biomarkers described herein, as well as kits and diagnostic methods comprising such antibodies and uses thereof.

The reference level of expression of a particular biomarker may be determined as a single value or a range of values which is/are determined based on the expression level of the biomarker measured, for instance, in a population of healthy subjects or in a population of subjects in need of therapy. According to certain embodiments of the present invention, the reference level of expression of a biomarker is determined based on the expression level of the biomarker measured in a population of subjects in need of a ziv-aflibercept therapy. The analyzed population may be divided into percentiles based on the measured level of expression of a particular biomarker. The reference level in some instances can be defined as the percentile that provides the best separation between patients suffering from a cancer on which the treatment with ziv-aflibercept is substantially effective as compared to patients suffering from a cancer for which treatment with ziv-aflibercept is less or sub-optimally effective. The reference level of expression of a particular biomarker may vary (i) according to the size of the studied population, and (ii) depending on the method used for measuring the expression of the biomarker.

VEGF Antagonists

As used herein, the expression "VEGF antagonist" means any molecule that blocks, reduces or interferes with the normal biological activity of vascular endothelial growth factor (VEGF) or a VEGF receptor. VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies (e.g., bevacizumab [AVASTIN®]), anti-VEGF receptor antibodies (e.g., anti-VEGFR1 antibodies, anti-VEGFR2 antibodies, etc.), and VEGF receptor-based chimeric molecules (also referred to herein as "VEGF-Traps").

VEGF receptor-based chimeric molecules include chimeric polypeptides which comprise two or more immunoglobulin (lg)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) (also known as aflibercept or ziv-aflibercept, and marketed under the product name ZALTRAP®) which is encoded by the nucleic acid sequence of SEQ ID NO: 1. VEGFR1R2-FcΔC1(a) comprises three components: (1) a VEGFR1 component comprising amino acids 27 to 129 of SEQ ID NO: 2; (2) a VEGFR2 component comprising amino acids 130 to 231 of SEQ ID NO: 2; and (3) a multimerization component ("FcΔC1(a)") comprising amino acids 232 to 457 of SEQ ID NO: 2 (the C-terminal amino acid of SEQ ID NO: 2 [i.e., K458] may or may not be included in the VEGF antagonist used in the methods of the invention; see e.g., U.S. Pat. No. 7,396,664). Amino acids 1-26 of SEQ ID NO: 2 are the signal sequence.

Biomarkers and Methods of Treatment of Metastatic Cancer

The present invention includes methods for treating cancer in a subject, e.g., advanced cancer, metastatic cancer, etc. The methods according to this aspect of the invention comprise administering a VEGF antagonist to the subject, wherein the subject has been diagnosed with cancer (e.g., metastatic colorectal cancer, advanced ovarian cancer) and has been selected for treatment with the VEGF antagonist on the basis of exhibiting elevated expression of a biomarker wherein the elevated expression of the biomarker is determined based on a comparison to the lower level of expression (i.e., reference level) of the respective biomarker in subjects with metastatic cancer. The VEGF antagonist may comprise a VEGF receptor-based chimeric molecule (VEGF Trap). An example of a VEGF Trap is ziv-aflibercept. In certain embodiments, the patient may be administered a VEGF antagonist in combination with a chemotherapeutic regimen comprising leucovorin (also known as folinic acid), 5 fluorouracil and irinotecan (the combination of which is referred to as "FOLFIRI").

The terms "subject" and "patient" are used interchangeably herein and refer to human subjects in need of treatment for a cancer, preferably metastatic cancer.

The present invention also includes methods for identifying a patient with metastatic colorectal cancer (mCRC) who is likely to respond favorably to anti-VEGF therapy. The methods comprise obtaining a sample from the patient and measuring in the sample the level of a biomarker such as VEGF-A, VEGF-R2, VEGF-R3, MIF and/or IL-8, wherein the elevated expression of the biomarker as compared to the lower level of expression (i.e., reference level) of the biomarker in subjects with mCRC, identifies the patient as a patient who is likely to respond favorably to anti-VEGF therapy. In alternate embodiments, the methods comprise obtaining a sample from the patient and measuring in the sample the level of a biomarker such as SPD, wherein lower expression of the biomarker as compared to the higher level of expression (i.e., reference level) of the biomarker in subjects with mCRC, identifies the patient as a patient who is likely to respond favorably to anti-VEGF therapy.

The present invention also includes methods for identifying a patient with advanced ovarian cancer who is likely to respond favorably to anti-VEGF therapy. The methods comprise obtaining a sample from the patient and measuring in the sample the level of a biomarker such as IL-6, wherein the variant expression of the biomarker as compared to the median level of expression (i.e., reference level) of the biomarker in subjects with ovarian cancer, identifies the patient as a patient who is likely to respond favorably to anti-VEGF therapy.

As used herein, a patient "likely to respond favorably" to anti-VEGF therapy refers to a patient having a cancer (e.g., mCRC, ovarian cancer) who upon administration of said anti-VEGF therapy is expected to show an effect selected from the group consisting of increased or improved overall survival as compared to a patient having the cancer and not on anti-VEGF therapy, increased progression-free survival, tumor regression, and decreased probability of tumor relapse. Improved survival time means about 1 week, 2 week, 4 week, 2 month, 4 month, 6 month, 8 month, 10 month, 12 month, 14 month, 16 month, 18 month, 20 month, 22 month, 24 month, 26 month, 28 month, 30 month, 36 month, 40 month, or longer survival as compared to similarly situated subjects with the cancer who do not receive anti-VEGF therapy.

The present invention also includes methods of determining prognosis of mCRC in a subject. The methods according to this aspect of the invention comprise obtaining a sample from the subject and measuring in the sample the level of a biomarker, wherein variant expression of the biomarker (elevated or reduced expression) as compared to the median level of expression of the respective biomarker in subjects with mCRC, identifies the patient as a patient with poor prognosis. In certain embodiments, the biomarker is selected from the group consisting of angiopoietin-2 (Ang-2) and C-reactive protein (CRP). In certain embodiments, reduced expression of a biomarker identifies the patient as a patient with good prognosis. In certain embodiments, good prognosis includes an effect selected from the group consisting of increased overall survival, progression-free survival, reduced tumor growth, tumor regression, and inhibition of tumor relapse in the patient. For example, in the present study, the inventors discovered that low plasma levels of Ang-2 or CRP correlated with higher probability of overall survival of a patient with mCRC.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Identification of Potential Predictive and Prognostic Biomarkers in Baseline Plasma Samples from a Phase 3 Clinical Trial of VEGF Trap in Patients with Metastatic Colorectal Cancer Introduction ZALTRAP® (ziv-aflibercept, also known as VEGF Trap), a VEGF-R1-R2-Fc chimeric protein that binds and neutralizes ligands of VEGFR1 and VEGFR2 (eg VEGF-A, PLGF, and VEGF-B), has been approved for the treatment of metastatic colorectal cancer (mCRC) (specifically in combination with FOLFIRI [a chemotherapeutic regimen comprising irinotecan, 5-fluorouracil, and leucovorin] in patients who have progressed after previous therapy including oxaliplatin).

Plasma and tumor samples were analyzed from a 1226-patient pivotal, randomized and placebo controlled registration trial of FOLFIRI +/−ziv-aflibercept (VELOUR, ClinicalTrials.gov Identifier: NCT00561470), in an effort to identify both prognostic and predictive factors. This Example sets forth an analysis of the baseline plasma samples, with the goal of identifying possible biomarkers of ziv-aflibercept response.

Results

A retrospective analysis of protein biomarkers from 553 baseline plasma samples was carried out. The population represented by the samples collected was similar to the overall VELOUR population. Samples were analyzed for levels of 98 analytes using multiplex immunoassays and ELISA. Biomarker values were dichotomized to biomarker "high" and "low" groups, based on the median value and then analyzed with respect to overall survival (OS) of the patient upon treatment.

For OS, the hazard ratio (HR) was 0.809 in the plasma biomarker population vs. HR=0.817 in the overall VELOUR population. For progression-free survival (PFS), the HR=0.752 in the plasma biomarker population vs. HR=0.758 in VELOUR. Patient demographics, including ECOG status, were similar between the groups. Several biomarkers were identified as potentially predictive or prognostic (or both) of OS, with a HR<0.7 (false discovery rate of 0.05 and interaction p<0.10). No biomarker subset corresponded to worse OS with ziv-aflibercept treatment.

Eight biomarkers were identified as potentially predictive of OS (Hazard Ratio (HR)<0.7; p<0.01, and were significant even after accounting for multiple testing), while 23 biomarkers were identified as potentially prognostic of OS (p<0.01). High levels of VEGF-A (at median=142 pg/mL) emerged as one of the potential predictive biomarkers of response to ziv-aflibercept therapy. Table 1 shows a primary analysis of the median overall survival of control and ziv-aflibercept-treated patients having high or low plasma VEGF-A levels.

TABLE 1

Primary analysis of the median overall survival of control and ziv-aflibercept-treated patients having high or low plasma VEGF-A levels

| | Median OS for Control (95% CI) | Median OS for ziv-aflibercept (95% CI) | HR (95% CI) | Log-rank test p-value |
|---|---|---|---|---|
| Total: Number of event, n/N (%) | 207/265 (78.1%) | 195/288 (67.7%) | | |
| VEGF (Low level): Number of event, n/N (%) | 95/132 (72%) | 96/142 (67.6%) | | |
| VEGF _(Low level) | 13.1 (10.8 to 17.1) | 12.8 (11.9 to 16.2) | 0.963 (0.725 to 1.28) | 0.7947 |
| VEGF (High level): Number of event, n/N (%) | 112/133 (84.2%) | 99/146 (67.8%) | | |
| VEGF _(High level) | 9.7 (8.5 to 11.3) | 12.5 (10.4 to 15.9) | 0.644 (0.49 to 0.845) | 0.0013 |

As shown in Table 1, patients with high plasma VEGF-A levels that were treated with ziv-aflibercept showed higher overall survival than control group. HR was calculated to be 0.644 (interaction p-value: 0.056) which indicated VEGF-A to be a potential predictive marker. Comparable results were shown with respect to PFS (HR=0.599, 95% CI: 0.453-0.792, p=0.001). Similarly, overall response rate (ORR) increased from 6.2% in the control group to 22.7% in the aflibercept-treated group in patients with high VEGF-A levels.

VEGF values within a range of 88-1140 pg/mL (categorized as "high") were used to determine cutoff values at 5% step-up increments. HR for OS was stable with VEGF cutoff level <222 pg/mL (FIG. 1). At higher VEGF levels (>335 pg/mL), the ziv-aflibercept effect was not as pronounced (highest 20% of patients).

VEGF pathway proteins VEGF-R2 and VEGF-R3 were identified as potential predictive biomarkers. Patients with high plasma sVEGF-R2 (median: 4.2 pg/mL) who were treated with ziv-aflibercept were potentially found to have better OS than control group (HR=0.686, 95% CI: 0.49-0.85, p=0.008). Comparable results were found with PFS (HR=0.679, 95% CI: 0.516-0.893, p=0.005). Patients with high plasma sVEGF-R3 (median: 35 pg/mL) who were treated with ziv-aflibercept were potentially found to have better OS than control group (HR=0.686; p=0.006). Comparable results were obtained for PFS (HR=0.711, 95% CI: 0.545-0.927, p=0.01).

Surfactant protein D (SPD) was identified as a potential predictive marker. Patients with low plasma SPD levels that were treated with ziv-aflibercept showed higher overall survival than control group (13.9 months as compared to 9.7 months; HR=0.598, 95% CI: 0.453-0.791, p value <0.001). Comparable results were seen for PFS (HR=0.581, 95% CI: 0.437-0.773, p value <0.001). Overall response rate increased from 8.1% in the control group to 25.6% in the aflibercept-treated group in patients with low SPD levels.

Macrophage Migration Inhibitory Factor (MIF) was identified as a potential predictive marker. Patients with high plasma MIF that were treated with ziv-aflibercept showed higher overall survival than control group (12.7 months as compared to 9.5 months; HR=0.67, 95% CI: 0.512-0.875, p value: 0.003). Similar results were shown with PFS (HR=0.607, 95% CI: 0.463-0.797, p value <0.001). Overall response rate increased from 10.5% in the control group to 20.9% in the aflibercept-treated group in patients with high plasma MIF levels.

Eotaxin-1 (CCL11) was identified as a potential predictive marker. Patients with high plasma eotaxin-1 that were treated with ziv-aflibercept showed higher probability of survival (HR: 0.661, 95% CI: 0.497-0.879; p-value 0.004). Similar results were shown with PFS (HR=0.701, 95% CI: 0.528-0.929, p value 0.012). Overall response rate increased from 8.7% in the control group to 23.3% in the aflibercept-treated group in patients with high plasma eotaxin-1 levels. In multivariate analyses, eotaxin-1 was predictive of response to ziv-aflibercept.

Some biomarkers were identified as potentially both predictive and prognostic. Interleukin-8 (IL-8) may be a predictive as well as a prognostic marker. Patients with low plasma IL-8 levels that were treated with ziv-aflibercept showed higher overall survival (9.4 months as compared to 8.0 months; HR=0.632, 95% CI: 0.489-0.817, p value: 0.0006) than control-treated patients. Comparable results were obtained for PFS (4.9 months as compared to 3.9 months) with HR=0.694, 95% CI: 0.534-0.902, p value: 0.005). IL-8 was also identified as a potential prognostic marker. Patients with low plasma IL-8 levels were found to have better OS (18.8 months as compared to 9.4 months for aflibercept-treated patients, HR=2.319, p=0; and 19.8 months as compared to 8.0 months for control, HR=4.48, p=0).

Figure 2:
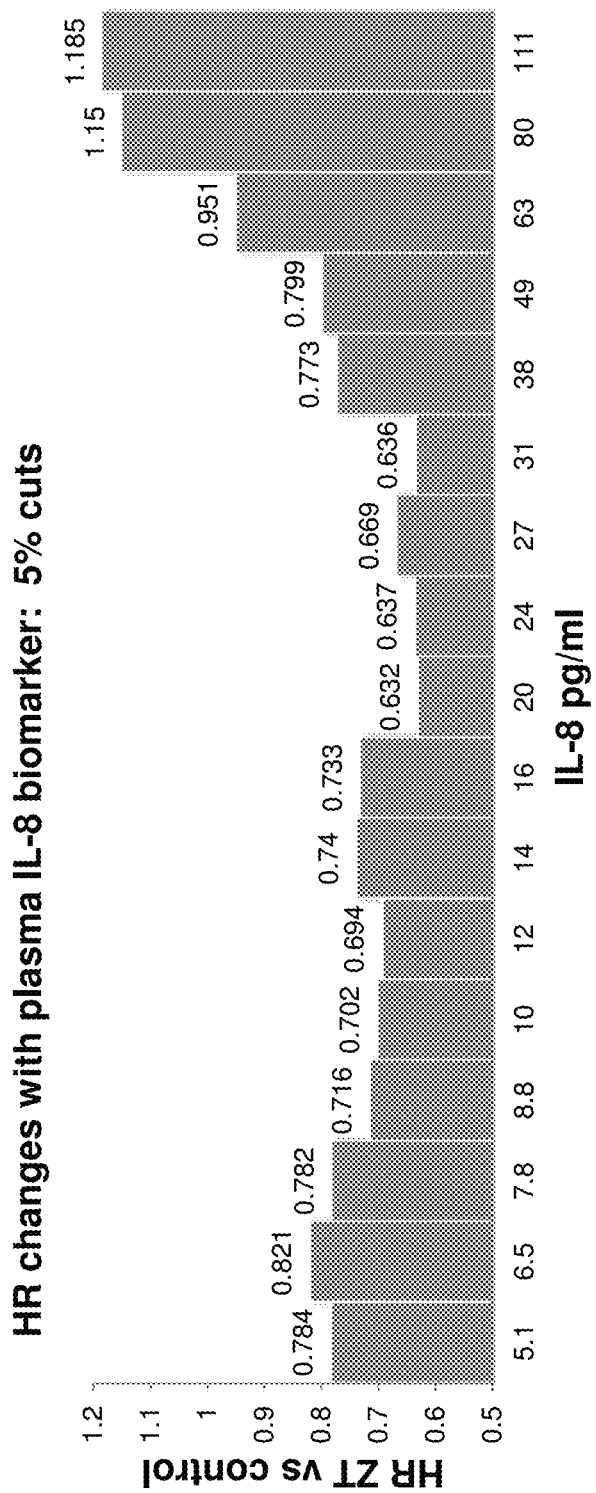
FIG. 2 is a graph of HR changes of the "high" biomarker group(s). The biomarker "high" group was defined by cutoff values ranging from 5.1 to 111 pg/mL of plasma IL-8 biomarker concentrations (in pg/mL) in a subset of patients with mCRC in a phase 3 study of mCRC patients treated with aflibercept in combination with FOLFIRI.

IL-8 values within a range of 5.1-111 pg/mL (categorized as "high") were used to determine cutoff values at 5% step-up increments. HR for OS was stable with IL-8 cutoff level <49 pg/mL (FIG. 2). The best HR was seen at levels between 20-31 pg/mL. At higher IL-8 levels (>63 pg/mL), the ziv-aflibercept effect was not as pronounced (highest 20% of patients).

Neuropilin-1 (NRP1) may be a prognostic marker. Patients with low plasma NRP1 were found to have better OS for aflibercept-treated patients (18.7 months as compared to 10.0 months, HR=2.104, p<0.001) and for control (14.2 months as compared to 9.0 months, HR=2.032, p<0.001).

Angiopoietin 2 (Ang-2) and C-reactive protein emerged as potential prognostic markers.

Table 2 shows primary analysis of the median overall survival of control and treated patients having high or low levels of Ang-2.

TABLE 2

Primary analysis of the median overall survival of control and treated patients having high or low levels of Ang-2

|  | Median OS for Control (95% CI) | Median OS for ziv-aflibercept (95% CI) | HR (95% CI) | Log-rank test p-value |
|---|---|---|---|---|
| Total: Number of event, n/N (%) | 207/265 (78.1%) | 195/288 (67.7%) |  |  |
| Ang-2 (Low level): Number of event, n/N (%) | 85/118 (72%) | 87/152 (57.2%) |  |  |
| Ang-2 (Low level) | 13.7 (11.7 to 17.7) | 18 (14.4 to 21.8) | 0.74 (0.549 to 0.998) | 0.0475 |
| Ang-2 (High level): Number of event, n/N (%) | 122/147 (83%) | 108/136 (79.4%) |  |  |
| Ang-2 (High level) | 9.6 (9 to 11.3) | 10.3 (8.5 to 12.2) | 0.892 (0.687 to 1.159) | 0.3894 |

Hepsin was identified as a potential predictive marker. Patients with high plasma hepsin that were treated with ziv-aflibercept showed higher probability of survival (HR: 0.671, 95% CI: 0.511-0.881; p-value 0.004). Similar results were shown with PFS (HR=0.661, 95% CI: 0.501-0.871, p value 0.003). Overall response rate increased from 10% in the control group to 22.5% in the aflibercept-treated group in patients with high plasma hepsin levels. In multivariate analyses, hepsin was predictive of response to ziv-aflibercept.

As shown in Table 2, patients with low plasma Ang-2 levels (<3.9 ng/mL) showed better survival outcomes than patients with high Ang-2 levels, regardless of treatment. High levels of Ang-2 correlated with a poor prognostic effect both in control and treated patient subsets (HR=1.83 in treated patients; HR=1.54 in control) (interaction p-value: 0.366). No statistically significant predictive effect was found to be associated with Ang-2 expression.

Table 3 shows primary analysis of the median overall survival of control and treated patients having high or low levels of CRP.

TABLE 3

Primary analysis of the median overall survival of control and treated patients having high or low levels of CRP

|  | Median OS for Control (95% CI) | Median OS for ziv-aflibercept (95% CI) | HR (95% CI) | Log-rank test p-value |
|---|---|---|---|---|
| Total: Number of event, n/N (%) | 207/265 (78.1%) | 195/288 (67.7%) | | |
| CRP (Low level): Number of event, n/N (%) | 85/131 (64.9%) | 76/145 (52.4%) | | |
| CRP __(Low level) | 17.4 (13.7 to 20.5) | 19.1 (16.7 to 25.1) | 0.765 (0.56 to 1.045) | 0.0905 |
| CRP (High level): Number of event, n/N (%) | 122/134 (91%) | 119/143 (83.2%) | | |
| CRP __(High level) | 8.6 (7.1 to 9.7) | 9.4 (7.8 to 11.5) | 0.763 (0.592 to 0.984) | 0.0354 |

As shown in Table 3, patients with low plasma CRP levels (<9.4 µg/mL) showed better survival outcomes than patients with high CRP levels, regardless of treatment. High levels of CRP correlated with a poor prognostic effect both in control and treated patient subsets (HR=2.553 in treated patients, $p<0.001$; and HR=2.773 in control, $p<0.001$). No predictive effect was found to be associated with CRP expression.

No biomarker subset corresponded to worse OS with ziv-aflibercept treatment.

Table 4 summarizes the top potential predictive marker results for aflibercept treatment.

TABLE 4

Top potential predictive marker results in the study

| Bio-marker | Median (min, max) | High or Low bio-marker group | Hazard Ratio (ZT vs. control) | P-value* | Inter-action P-value |
|---|---|---|---|---|---|
| IL-8 | 20 pg/mL (2, 4504 pg/mL) | High | 0.63 | 4.00E−04 | 0.022 |
| MIF | 0.3 ng/mL (0.015, 29 ng/mL) | High | 0.67 | 0.003 | 0.087 |
| Eotaxin-1 | 73 pg/mL (27-487 pg/mL) | High | 0.66 | 0.0041 | 0.087 |
| VEGF | 142 pg/mL (25, 2350 pg/mL) | High | 0.64 | 0.0013 | 0.056 |
| VEGFR2 | 4.2 ng/mL (1, 9 pg/mL) | High | 0.69 | 0.0082 | 0.157^ |
| VEGFR3 | 35 ng/mL (3, 125 pg/mL) | High | 0.69 | 0.0061 | 0.177^ |
| Hepsin | 771 pg/mL (190-1860 pg/mL) | High | 0.69 | 0.0038 | 0.06 |
| SPD | 7.7 ng/mL (0.19, 85 ng/mL) | Low | 0.60 | 3.00E−04 | 0.003 |

*Log rank P-values were adjusted for false discovery rate
^VEGF-R2 and VEGF-R3 fall below levels of significance

TABLE 5

Potentially prognostic markers in the study

| | | Control treated | | Ziv-aflibercept-treated | |
|---|---|---|---|---|---|
| Bio-marker | Median (min, max) | Hazard Ratio (High vs. Low) | P-value | Hazard Ratio (High vs. Low) | P-value |
| IL-8 | 20 pg/mL (2, 4504 pg/mL) | 4.4810 | <0.001 | 2.3189 | <0.001 |
| CRP | 9.4 mg/mL (6, 390 pg/mL) | 2.7732 | <0.001 | 2.5535 | <0.001 |
| NRP1 | 160 ng/mL (34, 387 ng/mL) | 2.0324 | <0.001 | 2.104 | <0.001 |
| ANG2 | 3.9 ng/mL (1, 59 pg/mL) | 1.5447 | 0.002 | 1.8293 | <0.001 |

Conclusions

In the present study, multiple predictive biomarkers of response to ziv-aflibercept have been identified including e.g., VEGF-A. Patients in the high VEGF-A group (i.e., plasma level >142 pg/mL) seemed to benefit the most from aflibercept treatment. Similar results were observed with VEGF-R2 and VEGF-R3. VEGF-R2 and VEGF-R3 may be of interest for further study as component of a signature. However, at the highest VEGF levels, the benefit was found to decline. In addition, several prognostic biomarkers were also identified in the course of the present analysis. Patient subsets with elevated expression of alternative angiogenic factors (e.g., Ang-2) or increased inflammatory markers, (e.g., CRP) correlated with poor outcome. Low NRP-1 may be a prognostic marker for survival. Samples containing high VEGF pathway markers also correlated with poor outcome in the absence of ziv-aflibercept treatment. Identification of the relevant pathways in patients will be important to optimize the efficacy of combination therapies.

Example 2: Identification of Potential Biomarkers in Serum Samples from a Phase 2 Clinical Trial of VEGF Trap in Patients with Ovarian Cancer In an international, double-blind, phase 2 study of advanced ovarian cancer (ClinicalTrials.gov Identifier: NCT00327171), aflibercept was used as a monotherapy. Patients received either a 2 mg/kg or 4 mg/kg dose of aflibercept every two weeks and were monitored for overall response. Serum samples were analyzed to identify potential predictive and prognostic markers. In this example, serum levels of interleukin-6 (IL-6) were measured in a subset of 96 patients.

Figure 3:
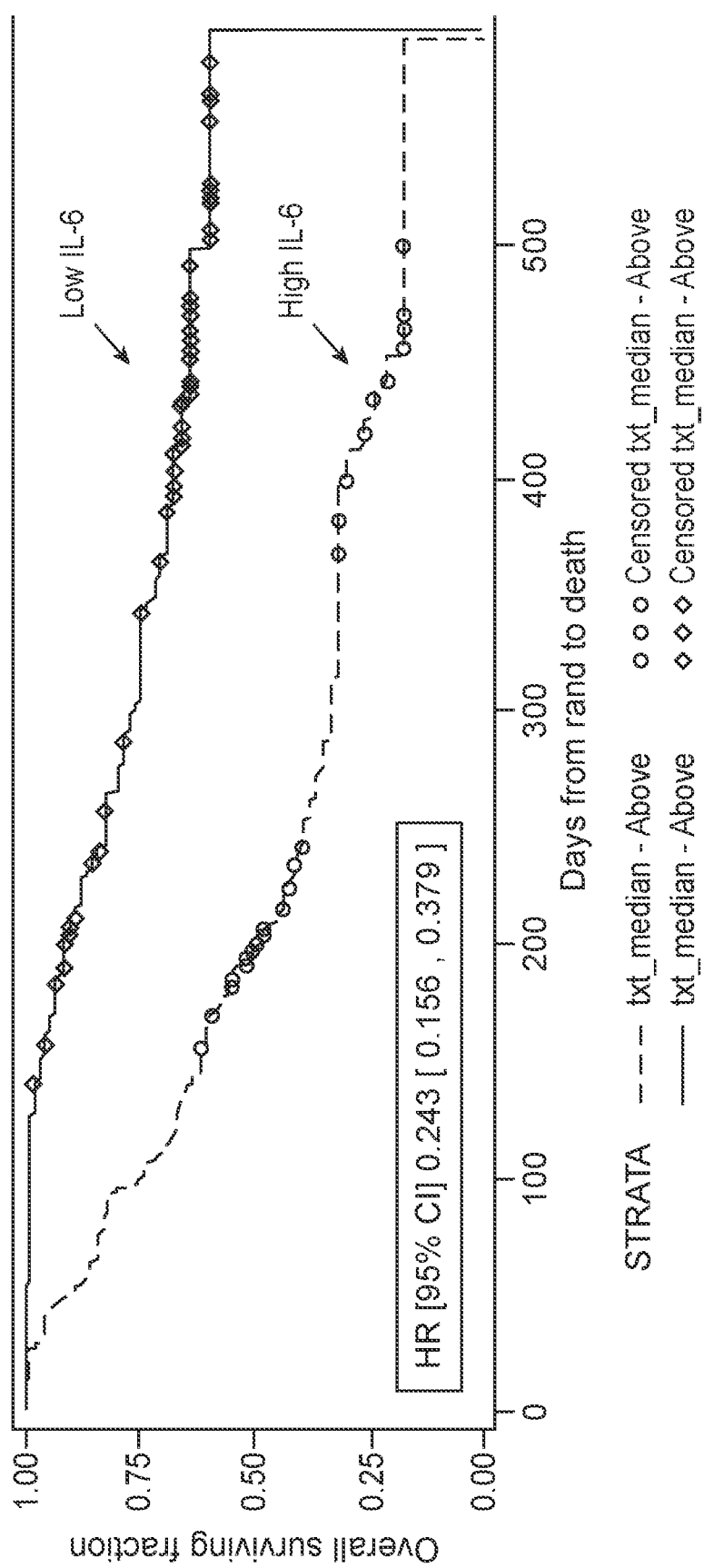
FIG. 3 shows correlation of high or low interleukin-6 (IL-6) levels with the overall surviving fraction of patients having ovarian cancer in a phase 2 study of advanced ovarian cancer patients treated with aflibercept monotherapy.

The study showed a modest response rate of 5% in both arms. When the data was stratified based on low (<median) and high (>median) IL-6 serum levels, it became apparent that patients with high IL-6 levels (>median) show a worse response (i.e., significantly poorer survival) compared to those with low IL-6 levels (<median) (FIG. 3). The results suggest a correlation between high levels of IL-6 and poorer response to anti-VEGF therapy. Elevated IL-6 levels may be a direct or indirect cause of resistance to anti-VEGF therapies observed in certain patients. Thus, the results of this Example suggest that screening cancer patients for elevated levels of IL-6 may identify certain patients whose therapeutic outcome would be enhanced by combining anti-VEGF therapy with anti-IL-6 or anti-IL-6R therapy, thereby counteracting or delaying the development of resistance to anti-VEGF therapies in these patients.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating metastatic colorectal cancer (mCRC) in a patient comprising administering a VEGF Trap that comprises Ig-like domain 2 of VEGFR1, Ig-like domain 3 of VEGFR2, and a multimerizing domain, to the patient,
   wherein the patient has been identified as likely to respond favorably to VEGF Trap therapy by a method comprising obtaining a sample from the patient and measuring in the sample the level of VEGF-A; wherein an elevated level of expression of VEGF-A identifies the patient as a patient who is likely to respond favorably to VEGF Trap therapy, and
   wherein the elevated expression of VEGF-A is determined based on a comparison to the lower level of VEGF-A in subjects with mCRC.

2. The method of claim 1, wherein the sample is blood, serum or plasma.

3. The method of claim 1, wherein the VEGF Trap is ziv-aflibercept.

4. The method of claim 3, wherein the expression level of VEGF-A is measured using an ELISA.

5. The method of claim 3 wherein the VEGF Trap therapy, further comprises:
   administering to the subject a chemotherapeutic regimen comprising irinotecan, 5-fluorouracil, and leucovorin (FOLFIRI).

6. The method of claim 1 wherein an elevated plasma level of expression of VEGF-A is determined to be at or above 88 pg/mL prior to treatment.

7. The method of claim 6, wherein the level of expression of VEGF-A is in a range of 88-1140 pg/mL.

8. The method of claim 6, wherein the VEGF-A level of expression is 142 pg/mL or higher.

* * * * *